United States Patent [19]
Johnson

[11] Patent Number: 5,637,600
[45] Date of Patent: Jun. 10, 1997

[54] PHENYLPYRROLE DERIVATIVES AND THEIR USE AS DOPAMINE $D_3$ ANTAGONISTS

[75] Inventor: Christopher N. Johnson, Essex, England

[73] Assignee: SmithKline Beecham p.l.c., England

[21] Appl. No.: 669,570

[22] PCT Filed: Feb. 16, 1995

[86] PCT No.: PCT/EP95/00580

§ 371 Date: Aug. 13, 1996

§ 102(e) Date: Aug. 13, 1996

[87] PCT Pub. No.: WO95/22542

PCT Pub. Date: Aug. 24, 1995

[30] Foreign Application Priority Data

Feb. 19, 1994 [GB] United Kingdom .......... 9403199

[51] Int. Cl.[6] ............ A61K 31/40; C07D 207/32
[52] U.S. Cl. ............ 514/326; 514/422; 514/423; 514/427; 514/689; 514/709; 546/208; 548/530; 548/560; 548/561; 568/31
[58] Field of Search ............ 514/422, 423, 514/427, 326, 689, 709; 546/208; 548/560, 561, 530; 568/31

[56] References Cited

FOREIGN PATENT DOCUMENTS

| | | |
|---|---|---|
| 0241053A1 | 10/1987 | European Pat. Off. . |
| 0259930A1 | 3/1988 | European Pat. Off. . |
| 0539281A1 | 4/1993 | European Pat. Off. . |
| WO94/03426 | 2/1994 | WIPO . |
| WO95/00508 | 1/1995 | WIPO . |

OTHER PUBLICATIONS

CA 124: 55790S Preparation of . . . antagonists. Johnson, p. 1212. 1996.

*Primary Examiner*—Joseph McKane
*Attorney, Agent, or Firm*—Nora Stein-Fernandez; William T. King; Edward T. Lentz

[57] ABSTRACT

The present invention relates to pyrrole compounds, processes for their preparation, pharmaceutical compositions containing them and their use in therapy, in particular as anti-psychotic agents.

12 Claims, No Drawings

PHENYLPYRROLE DERIVATIVES AND THEIR USE AS DOPAMINE D₃ ANTAGONISTS

This application is a 371 of PCT/EP95/00580 filed Feb. 16, 1995.

The present invention relates to novel pyrrole derivatives, processes for their preparation, pharmaceutical compositions containing them and their use in therapy, in particular as antipsychotic agents.

European Patent Application No. 241053, describes compounds of the formula:

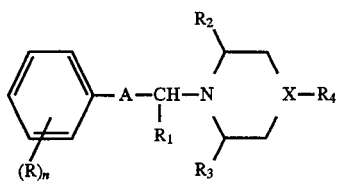

wherein A is an unsaturated 5-membered heterocyclic ring, such as 2,5-pyrrolyl, or 3,5- or 1,4- pyrazolyl; X is a nitrogen or carbon atom; $R_1$, $R_2$, $R_3$ are each hydrogen or alkyl; $R_4$ is aryl, heteroaryl, arylcarbonyl or heteroaryl-carbonyl; R is selected from a variety of substituents and n is 0–4. The compounds are said to have antipsychotic properties.

European Patent Application No. 259930 describes compounds of the formula:

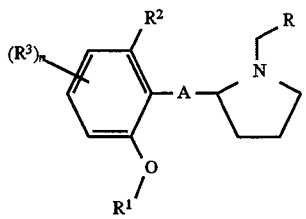

wherein A is an unsaturated 5-membered heterocyclic ring, such as 2,5-pyrrolyl, 1,4-pyrazolyl or 2,5-furyl; R is hydrogen, alkyl or optionally substituted phenyl; $R^1$ is alkyl, alkenyl or forms a ring with the phenyl group; $R^2$ is hydrogen, hydroxy or alkoxy; $R^3$ is selected from a variety of substituents and n is 0–3. These compounds are also said to have antipsychotic properties.

European Patent Application No. 539281 describes compounds of the formula:

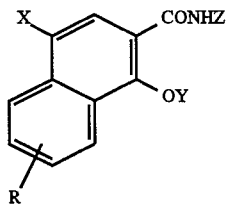

wherein Z is a residue derived from 2-aminomethyl-N-alkyl-pyrrolidine, 2-aminoethyl-N,N-diethylamine, 2-aminoethyl-morpholine, 2-aminoethyl-N,N-dibutylamine, 4-amino-N-butyl (or N-benzyl) piperidine or 2-aminoethyl-pyrrolidine; Y is alkyl or alkenyl; X is H, Cl, Br, amino, aminoalkyl, aminosulphamoyl, S-containing group (eg thiocyanato, alkylthio, alkylsulphinyl, alkylsulphonyl) methoxy, nitro, cyano, or an electron attracting group; and R is H or methoxy. The compounds are said to be dopamine antagonists, acting at the D₃ receptor and to be useful inter alia as antipsychotics.

We have now found novel pyrrole derivatives which have affinity for dopamine receptors and thus have potential as antipsychotic agents.

In a first aspect the present invention provides compounds of formula (I):

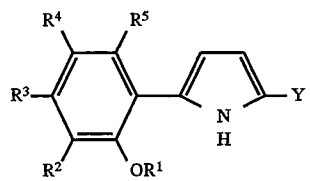

Formula (I)

wherein $R^1$ represents $C_1$-$C_4$alkyl;

$R^4$ represents a sulphonate group of formula $R^6OSO_2$ wherein $R^6$ is an optionally substituted aryl or optionally substituted heteroaryl group, $R^2$, $R^3$, and $R^5$ each independently represent hydrogen, halogen, $C_{1-4}$alkyl, $C_{1-4}$alkoxy, $C_{1-4}$alkoxy$C_{1-4}$alkyl, $C_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-$C_{1-4}$alkylamino, trifluoromethyl, trifluoromethoxy, hydroxyl, hydroxy$C_{1-4}$alkyl, $C_{1-4}$alkylthio, $C_{1-4}$alkanoyl or $C_{1-4}$alkoxycarbonyl; or $R^1$ and $R^2$ together form a $C_{2-4}$alkyl chain, which chain may be optionally substituted by one or two $C_{1-4}$alkyl groups, and $R^3$, $R^4$ and $R^5$ are as hereinbefore defined; or $R^2$ and $R^3$ together form a phenyl ring, $R^4$ represents a group $R^6OSO_2$— as defined above and $R^5$ represents hydrogen;

and Y represents a group selected from (a)–(e):

 (a)

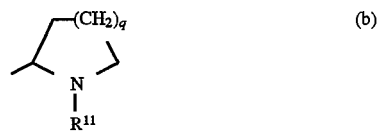 (b)

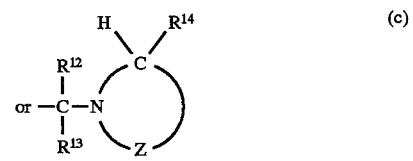 (c)

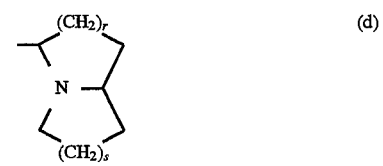 (d)

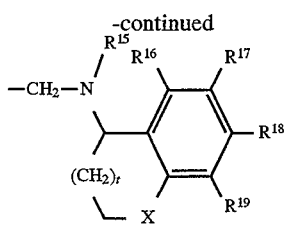

wherein in group (a):

R$^7$ and R$^8$ independently represent hydrogen, C$_{1-6}$alkyl, optionally substituted arylC$_{1-6}$alkyl or optionally substituted heteroarylC$_{1-6}$alkyl;

R$^9$ represents C$_{1-6}$alkyl, C$_{3-6}$alkenyl or C$_{3-6}$cycloalkylC$_{1-4}$alkyl; and R$^{10}$ represents C$_{1-6}$alkyl; C$_{3-6}$alkenyl; C$_{3-6}$cycloalkylC$_{1-4}$alkyl; optionally substituted arylC$_{1-4}$alkyl or optionally substituted heteroarylC$_{1-4}$alkyl; or NR$^9$R$^{10}$ forms a heterocyclic ring;

in group (b):

R$^{11}$ represents C$_{1-6}$alkyl; C$_{3-6}$alkenyl; C$_{3-6}$cycloalkylC$_{1-4}$alkyl, optionally substituted arylC$_{1-4}$alkyl or optionally substituted heteroarylC$_{1-4}$alkyl; and q is 1 to 4;

in group (c):

R$^{12}$ and R$^{13}$ independently represent hydrogen, C$_{1-6}$alkyl, optionally substituted arylC$_{1-6}$alkyl or optionally substituted heteroarylC$_{1-6}$alkyl;

R$^{14}$ represents an optionally substituted aryl or optionally substituted heteroaryl group; and Z represents —(CH$_2$)$_u$ wherein u is 2 to 8 or —(CH$_2$)$_v$CH=CH(CH$_2$)$_w$ where v and w independently represent 1 to 3;

in group (d) each of r and s independently represents an integer from 1 to 3;

and in group (e) R$^{15}$ represents C$_{1-6}$alkyl, C$_{3-6}$alkenyl or C$_{3-6}$cycloalkylC$_{1-4}$alkyl; and R$^{16}$, R$^{17}$, R$^{18}$ and R$^{19}$ each independently represent hydrogen, halogen, C$_{1-4}$alkyl, C$_{1-4}$alkoxy, C$_{1-4}$alkoxyC$_{1-4}$alkyl, nitro, cyano, trifluoromethyl, trifluoromethoxy, hydroxy, hydroxyC$_{1-4}$alkyl, C$_{1-4}$alkanoyl, C$_{1-4}$alkoxycarbonyl, amino or mono- or -di C$_{1-4}$alkylamino;

X is CH$_2$, S or O;

t is zero, 1 or 2; and salts thereof.

In the compounds of formula (I) an alkyl group or moiety may be straight or branched. Alkyl groups which may be employed include methyl, ethyl, n-propyl, n-butyl, n-pentyl, n-hexyl and any branched isomers thereof such as isopropyl, t-butyl, sec-pentyl, and the like.

A halogen atom present in the compounds of formula (I) may be fluorine, chlorine, bromine or iodine.

Representative aryl groups or moieties present in any of the substituents R$^2$, R$^3$, R$^4$, R$^5$, R$^6$, R$^7$, R$^8$, R$^{10}$, R$^{11}$, R$^{12}$, R$^{13}$ and R$^{14}$ in compounds of formula (I) include phenyl, naphthyl, and tetrahydronaphthyl. Suitable examples of heteroaryl groups include both 5 and 6-membered heterocycles containing one or more oxygen, sulphur or nitrogen atoms, such as furyl, thienyl, pyrrolyl, oxazolyl, thiazolyl, imidazolyl, oxadiazolyl, thiadiazolyl, pyridyl, pyridazyl, pyrimidyl and pyrazolyl. Substituents for said aryl and heteroaryl groups include halogen, C$_{1-4}$alkyl, C$_{1-4}$alkoxy, C$_{1-4}$alkoxyC$_{1-4}$alkyl, nitro, cyano, trifluoromethyl, trifluoromethoxy, hydroxy, hydroxyC$_{1-4}$alkyl, C$_{1-4}$alkanoyl, C$_{1-4}$alkoxycarbonyl, amino and mono- or -diC$_{1-4}$alkylamino.

When —NR$^9$R$^{10}$ forms a heterocyclic ring, this preferably has from 4 to 10, e.g. 5 to 8 ring members, and it may be fully or partially saturated. A heterocyclic ring —NR$^9$R$^{10}$ may also be bridged, for example by a C$_{1-3}$alkylene chain e.g. a methylene or ethylene group. Furthermore, the heterocyclic ring may be substituted by one or more C$_{1-4}$alkyl groups, or fused to an aromatic ring, such as phenyl.

R$^1$ preferably represents methyl or ethyl. R$^2$ preferably represents hydrogen. R$^3$ preferably represents hydrogen or methyl. R$^5$ preferably represents hydrogen. R$^6$ preferably represents phenyl.

When Y is a group (a) at least one of R$^7$ and R$^8$ is preferably hydrogen. Suitably one of R$^7$ and R$^8$ is hydrogen and the other is selected from hydrogen, C$_{1-6}$alkyl and optionally substituted arylC$_{1-6}$alkyl.

When Y is a group (b) q is preferably 1 or 2 and R$^{11}$ is preferably C$_{1-6}$alkyl, e.g. ethyl.

When Y is a group (c) at least one of R$^{12}$ and R$^{13}$ preferably represents hydrogen. Suitably one of R$^{12}$ and R$^{13}$ is hydrogen and the other is selected from hydrogen, C$_{1-6}$alkyl and optionally substituted arylC$_{1-6}$alkyl. R$^{14}$ preferably represents optionally substituted phenyl. Z preferably represents (CH$_2$)$_u$ wherein u is 3, 4 or 5.

When Y is a group (d) r and s preferably each independently represents 1 or 2.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulphuric, nitric or phosphoric acid; and organic acids eg. succinic, maleic, acetic, fumaric, citric, tartaric, benzoic, p-toluenesulphonic, methanesulphonic or naphthalenesulphonic acid. Other non-physiologically acceptable salts eg. oxalates, may be used, for example in the isolation of compounds of formula (I) and are included within the scope of this invention. Also included within the scope of the invention are solvates and hydrates of compounds of formula (I).

When an asymmetric centre is present in a compound of formula (I) the compound will exist in the form of optical isomers (enantiomers). The present invention includes within its scope all such enantiomers and mixtures, including racemic mixtures, thereof. In addition, all possible diastereomeric forms (individual diastereomers and mixtures thereof) of compounds of formula (I) are included within the scope of the invention.

Particular compounds according to the invention include:

2-(2-methoxy-5-phenoxysulfonylphenyl)-5-(1-[2-phenylazacycloheptyl]methyl)-1H-pyrrole;

2-(2-methoxy-4-methyl-5-phenoxysulphonylphenyl)-5-(1-(2-(R)-phenylazacycloheptyl)methyl)-1H-pyrrole;

2-(2-methoxy-5-phenoxysulphonylphenyl)-5-(1-(2-(R,S)-phenylpiperidinyl)methyl)-1H-pyrrole;

2-(2-(R,S)-(1-ethylpyrrolidinyl))-5-(2-methoxy-5-phenoxysulphonylphenyl)-1H-pyrrole;

2-(2-(R,S)-(1-ethylpyrrolidinyl))5-(2-methoxy-4-methyl-5-phenoxysulphonylphenyl)-1H-pyrrole;

2-(N-benzyl-N-ethyl)aminomethyl-5-(2-methoxy-5-phenoxysulphonylphenyl)-1H-pyrrole;

and salts thereof.

The present invention also provides a process for preparing compounds of formula (I) which process comprises:

(a) to prepare a compound of formula (I) wherein Y is a group (a) or (c) in which $R^7$, $R^8$, $R^{12}$ and $R^{13}$ are hydrogen or wherein Y is a group (e) carrying out a Mannich reaction with a compound of formula (II):

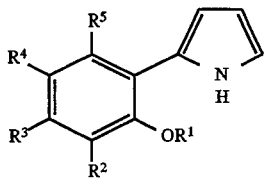

Formula II and an amine of formula (III), (IV) or (V):

HNR$^9$R$^{10}$  Formula (III)

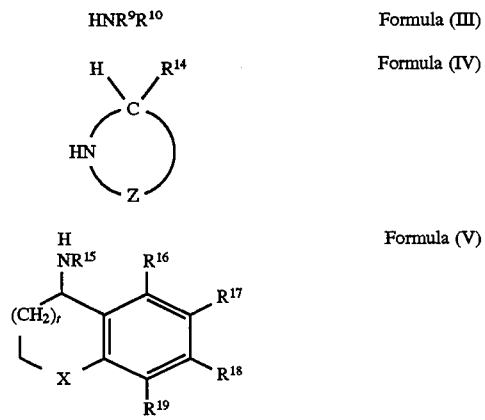

Formula (IV)

Formula (V)

in the presence of formaldehyde;

(b) to prepare a compound wherein Y is a group (a) wherein at least one of $R^7$ and $R^8$ is hydrogen, a group (c) wherein at least one of $R^{12}$ or $R^{13}$ is hydrogen, a group (e) or a group of formula (b) or (d) carrying out a Vilsmeier reaction with a compound of formula (II) and an amide of formula (VI), (VII) or (VIII):

$R^7C(O)NR^9R^{10}$  Formula (VI)

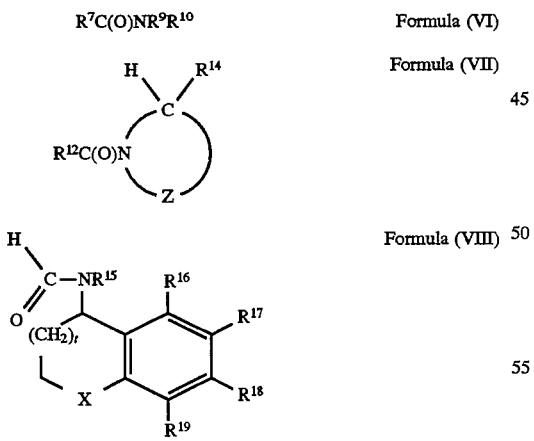

Formula (VII)

Formula (VIII)

or the appropriate oxo derivative of group (b) or (d) respectively, and reducing the intermediate product with, for example, sodium borohydride or cyanoborohydride;

(c) to prepare a compound wherein Y is a group (a) or (c) in which $R^7$, $R^8$, $R^{12}$ and $R^{13}$ are hydrogen or Y is a group (c) reductive amination of a compound of formula (IX):

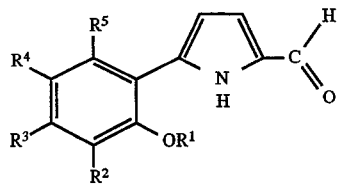

Formula IX with an amine of formula (III), (IV) or (V);

and optionally thereafter forming a salt of formula (I).

The Mannich reaction according to process (a) may be effected according to conventional methods. Thus for example the amine of formula (III), (IV) or (V) may first be reacted with formaldehyde and the product subsequently reacted with a compound of formula (II). The reaction is preferably effected in a protic solvent, for example an alcohol such as ethanol. An organic or inorganic acid, e.g. acetic acid may be employed as a catalyst.

The Vilsmeier reaction according to process (b) may also be effected according to conventional methods. Thus, for example, the amide of formula (VI) (VII) or (VIII) or the oxo derivative of group (b) or (d) may first be reacted with phosphorus oxychloride and the resulting product subsequently reacted with a compound of formula (II), conveniently in a solvent such as dichloromethane or dichloroethane. The product of this reaction is then reduced with, for example, sodium borohydride or cyanoborohydride. The reduction may be carried out in a suitable solvent, for example dichloroethane, dichloromethane, methanol, ethanol, water or mixtures thereof.

Reductive amination according to process (c) will generally be carried out using a reducing agent such as sodium borohydride or cyanoborohydride and in the presence of a Lewis acid such as titanium (IV) chloride. Reaction of a compound (IX) with the amine may conveniently be effected in a solvent such as dichloromethane or dichloroethane.

A compound of formula (II) may be prepared by cyclisation of a dicarbonyl compound of formula (X):

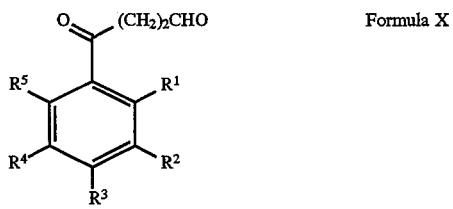

Formula X

The reaction may be effected using an ammonium salt, e.g. ammonium acetate, in a solvent such as ethanol. (See, for example, C. G. Kruse et at., Heterocycles, vol 26, P3141, 1987).

A compound of formula (X) may itself be prepared by reacting the appropriate substituted aroyl halide with a metallo derivative of a 2-(2-haloethyl)-1,3-dioxolane or 2-(2-haloethyl)-1,3-dioxane and subsequent acid hydrolysis.

Compounds of formulae (III) and (IV) are available commercially or may be prepared by standard methods.

An amine (V) may be obtained by reductive amination of a ketone of formula (XI):

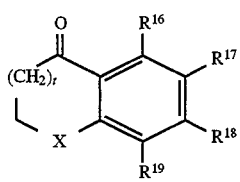

Formula (XI)

with an amine $R^{15}NH_2$, in the presence of a titanium (IV) chloride followed by reduction with e.g. sodium cyanoborohydride, as described above for process (c).

Compounds of formula (VI) and (VII) wherein $R^7$ and $R^{12}$ respectively are other than hydrogen may be prepared by acylation of the appropriate amine of formula (III) or (IV), for example using the corresponding acyl halide.

Compounds of formula (VI) and (VII) where $R^7$ and $R^{12}$ respectively represent hydrogen, as well as compounds (VIII) may be prepared by reacting the appropriate amine of formula (III), (IV) or (V) with a formylating agent, for example acetic anhydride in formic acid.

A compound of formula (IX) may be prepared by carrying out a Vilsmeier reaction in which dimethylformamide is reacted with phosphorus oxychloride and the product reacted with a compound of formula (II), in a solvent such as dichloroethane, followed by acid hydrolysis.

Substituents $R^1$ to $R^5$ may be introduced at any appropriate stage of the synthesis, preferably at an early stage prior to formation of the pyrrole moiety, using methods known in the art. Thus, for example the substituent $R^6OSO_2$— may be formed by reaction of a compound of formula (XII).

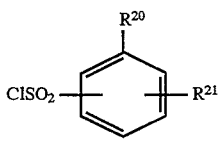

Formula (XII)

(wherein $R^{20}$ represents a carboxyl group or a halogen atom e.g. bromine and $R^{21}$ represents optional ring substituents selected from $OR^1$, $R^2$, $R^3$ and $R^5$) with a compound $R^6OH$. The reaction may conveniently be effected in the presence of a solvent e.g. tetrahydrofuran or water and optionally in the presence of a base. Compounds of formula (XII) are known (e.g. German OLS 2,721,643) or may be prepared by standard methods.

If necessary, groups or moieties present in any of the substituents $R^1$ to $R^5$ or in the group Y which may be sensitive to any of the reactions used in preparation of compounds (I) may be protected during the reaction by methods well known in the art and the protecting groups removed at any convenient stage in the synthesis, for example at the final stage, by standard procedures.

When a compound of formula (I) is obtained as a mixture of enantiomers these may be separated by conventional methods such as crystallisation in the presence of a resolving agent, or chromatography, for example using a chiral HPLC column.

Alternatively a compound of formula (I) may be prepared as a single enantiomer by employing a chiral amine in the synthesis, for example directly in process (a) or (c) or in the preparation of an amide for use in process (b). A chiral amine of formula (III), (IV) or (V) may be prepared by resolving an enantiomeric mixture of the appropriate amine for example by coupling to a chiral auxiliary such as (S)-(+)-α-methoxyphenylacetic acid and separating the resulting diastereoisomers by chromatography. The auxiliary moiety may be removed by standard methods to give the desired chiral amine. Thus for example the (S)-(+)-α-methoxyphenylacetyl moiety may be cleaved under basic conditions.

Compounds of formula (I) have been found to exhibit affinity for dopamine receptors, in particular the $D_3$ receptor, and are expected to be useful in the treatment of disease states which require modulation of such receptors, such as psychotic conditions. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant eps. (see for example Sokoloff et al, Nature, 1990; 347:146–151; and Schwartz et al, Clinical Neuropharmacology, Vol 16, No. 4, 295–314, 1993). Preferred compounds of the present invention are therefore those which have higher affinity for dopamine $D_3$ than dopamine $D_2$ receptors (such affinity can be measured using standard methodology for example using cloned dopamine receptors). Said compounds may advantageously be used as selective modulators of $D_3$ receptors. In particular compounds of formula (I) are dopamine $D_3$ receptor antagonists and as such are of potential use as antipsychotic agents for example in the treatment of schizophrenia, schizo-affective disorders, psychotic depression and mania. Other conditions which may be treated by modulation of dopamine $D_3$ receptors include dyskinetic disorders such as Parkinson's disease, neuroleptic-induced parkinsonism and tardive dyskinesias; depression; and drug (eg. cocaine) dependency.

In a further aspect therefore the present invention provides a method of treating conditions which require modulation of dopamine $D_3$ receptors, for example psychoses such as schizophrenia, which comprises administering to a subject in need thereof an effective mount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine $D_3$ receptors, for example psychoses such as schizophrenia.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

The invention is further illustrated by the following non-limiting examples:

DESCRIPTION 1

2-Methoxy-5-Phenoxysulfonylbenzoic acid

To a rapidly stirred mixture of 2-methoxy-5-chlorosulfonylbenzoic acid (5.0 g, 20 mmol) and phenol (1.88 g, 20 mmol) in water (100 mL) was added dropwise a solution of sodium hydroxide (16 mL, 10%; 40 mmol) over 10 min. The mixture was stirred for 18 h, and then extracted with ether. The aqueous phase was acidified to pH 1 with conc. HCl and the white precipitate filtered off to give the title compound (4.05 g).

$^1$H NMR (CDCl$_3$)ϵ 4.03 (3H, s), 5.60 (1H, br s), 7.00 (2H, m), 7.08 (1H, d, J=8 Hz), 7.30 (3H, m), 7.87 (1H, dd, J=8, 2 Hz), 8.39 (1H, d, J=2 Hz).

DESCRIPTION 2

2-Methoxy-5-Phenoxysulfonylbenzoyl chloride

To a suspension of 2-methoxy-5-phenoxysulfonylbenzoic acid (4.0 g, 13 mmol) in dry toluene (100 mL) was added oxalyl chloride (2.3 mL, 26 mmol) at room temperature. A drop of DMF was added and the mixture stirred at room temperature for 2 h. The mixture was evaporated in vacuo and the residue triturated with 1:1 toluene/hexane to give the title compound as a solid (4.04 g).

$^1$H NMR (CDCl$_3$)ϵ 4.04 (3H, s), 7.02 (2H, m), 7.11 (1H, d, J=8 Hz), 7.32 (3H, m), 8.00 (1H, dd, J=8, 2 Hz), 8.45 (1H, d, J=2 Hz)

DESCRIPTION 3

2-(2-Methoxy-5-Phenoxysulfonylphenyl)-1H-pyrrole

Prepared from 2-methoxy-5-phenoxysulfonylbenzoyl chloride (D2) (4.04 g, 12 mmol) by the method of Kruse et al (Heterocycles, 26, 3141, 1987).

$^1$H NMR (CDCl$_3$)ϵ 4.05 (3H, s), 6.30 (1H, m), 6.62 (1H, m), 6.91 (1H, m), 7.02 (3H, m), 7.27 (3H, m), 7.57 (1H, dd, J=8, 2 Hz), 8.05 (1H, d, J=2 Hz), 9.68 (1H, br,s).

DESCRIPTION 4

1-Formyl-2-(R,S)-phenylazacycloheptane

To a mixture of, 98–100% formic acid (30 ml) and acetic anhydride (100 ml) was added 2-(R,S)-phenylazacycloheptane (10 g, 57.1 mmol; B. E. Maryanoff et al., J.Med. Chem., 30, 1433, 1987) and the mixture warmed to 70° C. for 2 h. The reaction mixture was then cooled and evaporated to dryness in vacuo and the residue was partitioned between ether and saturated aqueous potassium carbonate. The ether layer was separated and evaporated to dryness in vacuo to afford the title compound (11.24 g; 97%) as a mixture of E/Z isomers.

$^1$H NMR (CDCl$_3$) exists as two isomers; ϵ 1.2–2.1(7H, m), 2.3–2.6 (1H, m), 2.8 (t, J=12 Hz) and 3.3 (t, J=12 Hz) (together 1H), 3.65 (br d, J=12 Hz) and 4.24 (br d, J=12 Hz) (together 1H), 4.67 (q, J=7 Hz) and 5.3 (q, J=7 Hz) (together1H), 7.13–7.45, (5H, m), 8.15 (s) and 8.3 (s) (together 1H).

DESCRIPTION 5

2-Methoxy-4-methyl-5-phenoxysulfonylbenzoic acid.

Prepared from 2-methoxy-4-methyl-5-chlorosulphonylbenzoic acid according to the method of description 1, in 49% yield.

$^1$H NMR (CDCl$_3$)ϵ:2.83 (3H, s), 4.12 (3H, s), 7.01 (3H, m), 7.19–7.35 (3H, m) 8.56 (1H, s).

DESCRIPTION 6

2-(2-Methoxy-4-methyl-5-phenoxysulphonylphenyl)-1H-pyrrole.

Prepared from 2-methoxy-4-methyl-5-phenoxysulphonylbenzoic acid according to the methods of descriptions 2 and 3, in 46% overall yield.

$^1$H NMR (CDCl$_3$)ϵ: 2.71 (3H, s), 4.05 (3H, s), 6.25 (1H, m), 6.57 (1H, m), 6.87 (1H, m), 6.91 (1H, s), 7.02 (2H, m), 7.16–7.84 (3H, m), 8.05 (1H, s), 9.58 (1H, br s).

DESCRIPTION 7

1-Formyl-2-(R)-phenylazacycloheptane.

Prepared according to the general method of Description 4.

$^1$H NMR (CDCl$_3$) exists as two isomers, ϵ: 1.19–2.09 (7H, m), 2.39 (m) and 2.57 (m) (together 1H), 2.81 (t, J=13 Hz) and 3.34 (t, J=13 Hz) (together 1H), 3.68 (broad d, J=13 Hz) and 4.24 (broad d, J=13 Hz) (together 1H), 4.68 (q, J=7 Hz) and 5.31 (q, J=7 Hz (together 1H), 7.13–7.50 (5H, m), 8.15 (s) and 8.29 (s) (together 1H).

DESCRIPTION 8

1-Formyl-2-(R,S)-phenylpiperidine

Prepared from 2-(R,S)-phenylpiperidine according to the method of Description 4.

$^1$H NMR (CDCl$_3$) exists as a mixture of E/Z isomers ϵ:1.40–2.10 (5H, m), 2.33–2.53 (1H, m), 2.85–3.17 (1H, m), 3.46 (m) and 4.10 (m) (together 1H), 4.77 (m) and 5.75 (m) (together 1H), 7.10–7.53 (5H, m), 8.14 (s) and 8.25 (s) (together 1H).

EXAMPLE 1

2-(2-Methoxy-5-Phenoxysulfonylphenyl)-5-(1-[2-phenylazacycloheptyl]methyl)-1H-pyrrole, hydrochloride 1-Formyl-2-phenylazacycloheptane (1.02 g, 5 mmol) was treated with phosporus oxychloride (0.45 mL, 5 mmol) at 0° C., under argon, with stirring. After warming to room temperature and dilution with 1,2-dichloroethane (10 mL), a solution of 2-(2-methoxy-5-phenoxysulfonyl)phenyl-1H-pyrrole (1.13 g, 3.4 mmol) in 1,2 dichloroethane (20 mL) was added and the reaction stirred at room temperature for 18 h. The reaction mixture was cooled to 0° C., and then sodium borohydride (1.0 g) added portionwise. After stirring for 1 h, methanol (5 mL) was added dropwise, followed by water (5 mL), and the mixture partitioned between water and saturated aqueous potassium carbonate. The organic phase was separated, dried and evaporated in vacuo, and the residue treated with conc. HCl (5 mL) and methanol (5 mL) over 2 h. The resulting solution was partitioned between aqueous sodium hydroxide (10%; 50 mL) and dichloromethane (3×50 mL). The combined organic extracts were dried and evaporated in vacuo. Chromatography (SiO$_2$, eluant 10–20% EtOAc-hexane) gave a gum (1.21 g) which was converted to the HCl salt by treatment with aqueous dil. HCl and extraction into dichloromethane to give the title compound (E1).

Analysis: Found, C 64.85%, H 6.05%, N 5.12%, C$_{30}$H$_{32}$N$_2$O$_4$S.HCl requires C 65.15%, H 6.01%, N 5.06%.

The following compounds were prepared from the corresponding pyrrole according to the procedure of Example 1:

2-(2-Methoxy-4-methyl-5-phenoxysulphonylphenyl)-5-(1-(2-(R)-phenylazacyclohepty)methyl)-1H-pyrrole hydrochloride.

Mass Spectrum: Found M$^+$530.2237. C$_{31}$H$_{34}$N$_2$O$_4$S requires M$^+$530.2239.

2-(2-Methoxy-5-phenoxysulphonylphenyl)-5-(1-(2-(R,S)-phenylpiperidinyl)methyl)-1H-pyrrole hydrochloride.

$^1$H NMR (CDCl$_3$)ϵ: 1.63 (1H, m), 1.75–2.13 (3H, m), 2.23–2.73 (3H, m), 3.40–3.62 (2H, m), 3.82 (1H, m), 4.18 (3H, s), 4.25 (1H, m), 6.15 (1H, m), 6.45 (1H, m) 6.90–7.08 (3H, m), 71.8–7.60 (7H, m), 7.88 (2H, br s), 8.03 (1H, d, J=3 Hz), 11.34 (1H, br s), 12.45 (1H, br s).

EXAMPLE 2

2-(2-(R,S)-(1-Ethylpyrrolidinyl))-5-(2-methoxy-5-phenoxysulphonylphenyl)-1H-pyrrole hydrochloride.

Prepared from 2-(2-Methoxy-5-phenoxysulphonylphenyl)-1H-pyrrole and 1-ethyl-2-pyrrolidinone by a similar procedure to that described in Example 1, in 69% yield. Mass Spectrum: Found M$^+$426.1607. C$_{23}$H$_{26}$N$_2$O$_4$S requires M$^+$426.1606.

Similarly prepared from the corresponding pyrrole according to the procedure of Example 2 was:

2-(2-(2-(R,S)-(1-Ethylpyrrolidinyl))5-(2-methoxy-4-methyl-5-phenoxysulphonylphenyl)-1H-pyrrole hydrochloride Found: C, 60.0; H, 6.1; N, 5.8. C$_{24}$H$_{28}$N$_2$O$_4$S.HCl requires C, 60.4; H, 6.1; N, 5.9%.

EXAMPLE 3

2-(N-Benzyl-N-ethyl)aminomethyl-5-(2-methoxy-5-phenoxysulphonylphenyl)-1H-pyrrole hydrochloride To a stirred solution of N-ethylbenzylamine (0.17 ml, 0.15 g, 1.1 mmol) in ethanol (10 ml) at room temperature under argon was added 40% aqueous formaldehyde (0.08 ml, 1.1 mmol) followed by glacial acetic acid (0.11 ml, 1.4 mmol). The resulting mixture was stirred for 0.5 h then 2-(2-methoxy-5-phenoxysulphonylphenyl)-1H-pyrrole (0.33 g, 1.0 mmol) was added in one portion. Stirring was continued for 72 h, then excess ethanol was evaporated in vacuo. The residue was partitioned between saturated aqueous NaHCO$_3$ (50 ml) and dichloromethane (3×50 ml) and the combined organic extracts dried and evaporated in vacuo to give an oil (0 6 g). Chromatography on silica gel, gradient eluting with hexane/ethyl acetate gave the free base as an oil (0 36 g). Treatment with ethereal HCl in dichloromethane gave the title compound.

$^1$H NMR (CDCl$_3$)ϵ: 1.21 (3H, t, J=7 Hz), 2.96 (2H, m), 3.80–4.00 (1H, m), 4.22 (3H, s), 4.15–4.52 (3H, m), 6.29 (1H, m), 6.51 (1H, m), 6.88–7.12 (3H, m), 7.15–7.80(9H, m), 8.06 (1H, d, J=3 Hz), 11.80 (1H, br s), 12.28 (1H, br s).

Biological Test Methods

The ability of the compounds to bind selectively to human D$_3$ dopamine receptors can be demonstrated by measuring their binding to cloned receptors. The inhibition constants (K$_i$) of test compounds for displacement of [$^{125}$I] iodosulpride binding to human D$_3$ dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −40° C. Crude cell membranes were prepared by homogenisation followed by high-speed centrifugation, and characterisation of cloned receptors achieved by radioligand binding.

Preparation of CHO cell membranes

Cell pellets were gently thawed at room temperature, and resuspended in about 20 volumes of ice-cold 50 mM Tris salts (pH 7.4@37° C.), 20 mM EDTA, 0.2M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4@37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4@37° C.). The final pellet was resuspended in 50 mM Tris salts (pH 7.4@37° C.), and the protein content determined using bovine serum albumin as a standard (Bradford, M. M. (1976) Anal. Biochem. 72, 248–254).

Binding experiments on cloned dopamine receptors

Crude cell membranes were incubated with 0.1 nM [$^{125}$I] iodosulpride (~2000 Ci/mmol; Amersham, U. K.), and the test compound in a buffer containing 50 mM Tris salts (pH 7.4@37° C.), 120 mM NaCl, 5 mM KCl, 2 mM CaCl$_2$, 1 mM MgCl$_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4@37° C.), 120 mM NaCl, 5 mM KCl, 2 mM CaCl$_2$, 1 mM MgCl$_2$. The radioactivity on the filters was measured using a Cobra gamma counter (Canberra Packard). Non-specific binding was defined as the radioligand binding remaining after incubation in the presence of 100 μM iodosulpride. For competition curves, 14 concentrations (half-log dilutions) of competing cold drug were used.

Competition curves were analysed simultaneously whenever possible using non-linear least-squares fitting procedures, capable of fitting one, two or three site models.

Compounds of Examples 1 to 3 had IC$_{50}$ values of between 5 and 20 nM at the human D$_3$ receptor.

Pharmaceutical Formulations

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |
| Buffer: | Suitable buffers include citrate, phosphate, sodium hydroxide/hydrochloric acid. |
| Solvent: | Typically water but may also include cyclodextrins (1–100 mg) and co-solvents such as propylene glycol, polyethylene glycol and alcohol. |
| Tablet | |
| Compound | 1–40 mg |
| Diluent/Filler* | 50–250 mg |
| Binder | 5–25 mg |
| Disentegrant* | 5–50 mg |
| Lubricant | 1–5 mg |

| —continued | |
|---|---|
| Cyclodextrin | 1–100 mg |
| Diluent: | e.g. Microcrystalline cellulose, lactose, starch |
| Binder: | e.g. Polyvinylpyrrolidone, hydroxypropylmethylcellulose |
| Disintegrant: | e.g. Sodium starch glycollate, crospovidone |
| Lubricant: | e.g. Magnesium stearate, sodium stearyl fumarate. |
| Oral Suspension | |
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |
| Suspending agent: | e.g. Xanthan gum, microcrystalline cellulose |
| Diluent: | e.g. sorbitol solution, typically water |
| Preservative: | e.g. sodium benzoate |
| Buffer: | e.g. citrate |
| Co-solvent: | e.g. alcohol, propylene glycol, polyethylene glycol, cyclodextrin |

*may also include cyclodextrins

I claim:

1. A compound of formula (I):

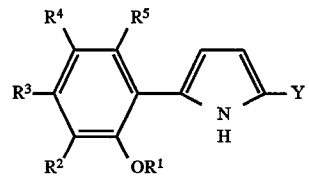

Formula (I)

wherein

R$^1$ represents C$_{1-4}$alkyl;

R$^4$ represents a sulphonate group of formula R$^6$OSO$_2$ wherein R$^6$ is an optionally substituted aryl or optionally substituted heteroaryl group, R$^2$, R$^3$ and R$^5$ each independently represent hydrogen, halogen, C$_{1-4}$alkyl, C$_{1-4}$alkoxy, C$_{1-4}$alkoxyC$_{1-4}$alkyl, C$_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-C$_{1-4}$alkylamino, trifluoromethyl, trifluoromethoxy, hydroxyl, hydroxyC$_{1-4}$alkyl, C$_{1-4}$alkylthio, C$_{1-4}$alkanoyl or C$_{1-4}$alkoxycarbonyl; or R$^1$ and R$^2$ together form a C$_{2-4}$alkyl chain, which chain is optionally substituted by one or two C$_{1-4}$alkyl groups, and R$^3$, R$^4$ and R$^5$ are as hereinbefore defined; or R$^2$ and R$^3$ together form a phenyl ring, in which case R$^4$ represents a group R$^6$OSO$_2$— as defined above and R$^5$ represents hydrogen;

and Y represents a group selected from (a)–(e):

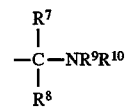

(a)

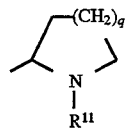

(b)

-continued

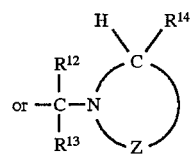  (c)

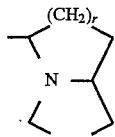  (d)

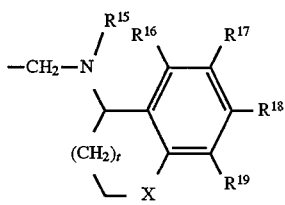  (e)

wherein in group (a):
R$^7$ and R$^8$ independently represent hydrogen, C$_{1-6}$alkyl, optionally substituted arylC$_{1-6}$alkyl or optionally substituted heteroarylC$_{1-6}$alkyl;

R$^9$ represents C$_{1-6}$alkyl, C$_{3-6}$alkenyl or C$_{3-6}$cycloalkylC$_{1-4}$alkyl; and R$^{10}$ represents C$_{1-6}$alkyl; C$_{3-6}$alkenyl; C$_{3-6}$cycloalkylC$_{1-4}$alkyl, optionally substituted. arylC$_{1-4}$alkyl or optionally substituted heteroarylC$_{1-4}$alkyl; or NR$^9$R$^{10}$ forms a heterocyclic ring;

in group (b):
R$^{11}$ represents C$_{1-6}$alkyl; C$_{3-6}$alkenyl; C$_{3-6}$cycloalkylC$_{1-4}$alkyl, optionally substituted arylC$_{1-4}$alkyl or optionally substituted heteroarylC$_{1-4}$alkyl; and
q is 1 to 4;

in group (c):
R$^{12}$ and R$^{13}$ independently represent hydrogen, C$_{1-6}$alkyl, optionally substituted arylC$_{1-6}$alkyl or optionally substituted heteroarylC$_{1-6}$alkyl;

R$^{14}$ represents an optionally substituted aryl or optionally substituted heteroaryl group; and Z represents —(CH$_2$)$_u$ wherein u is 2 to 8 or —(CH$_2$)$_v$CH=CH(CH$_2$)$_w$ where v and w independently represent 1 to 3;

in group (d) each of r and s independently represents an integer from 1 to 3;

and in group (e) R$^{15}$ represents C$_{1-6}$alkyl, C$_{3-6}$alkenyl or C$_{3-6}$cycloalkylC$_{1-4}$alkyl; and R$^{16}$, R$^{17}$, R$^{18}$ and R$^{19}$ each independently represent hydrogen, halogen, C$_{1-4}$alkyl, C$_{1-4}$alkoxy, C$_{1-4}$alkoxyC$_{1-4}$alkyl, nitro, cyano, trifluoromethyl, trifluoromethoxy, hydroxy, hydroxyC$_{1-4}$alkyl, C$_{1-4}$alkanoyl, C$_{1-4}$alkoxycarbonyl, amino or mono- or -di C$_{1-4}$alkylamino;

X is CH$_2$, S or O;

t is zero, 1 or 2;

or a salt thereof.

2. A compound according to claim 1 wherein R$^1$ represents methyl or ethyl.

3. A compound according to claim 1 which is selected from the group consisting of:

2-(2-methoxy-5-phenoxysulfonylphenyl)-5-(1-[2-phenylazacycloheptyl]methyl)-1H-pyrrole;

2-(2-methoxy-4-methyl-5-phenoxysulphonylphenyl)-5-(1-(2-(R)phenylazacycloheptyl) methyl)-1H-pyrrole;

2-(2-methoxy-5-phenoxysulphonylphenyl)-5-(1-(2-(R,S)-phenylpiperidinyl)methyl)1H-pyrrole;

2-(2-(R,S)-(1-ethylpyrrolidinyl))-5-(2-methoxy-5-phenoxysulphonylphenyl)-1H-pyrrole;

2-(2-(R,S)-(1-ethylpyrrolidinyl))5-(2-methoxy-4-methyl-5-phenoxysulphonylphenyl)-1H-pyrrole; and 2-(N-benzyl-N-ethyl)aminomethyl-5-(2-methoxy-5-phenoxysulphonylphenyl)-1H-pyrrole;

or a salt thereof.

4. A process for preparing a compound of formula (I) which process comprises:

(a) to prepare a compound of formula (I) wherein Y is a group (a) or (c) in which R$^7$, R$^8$, R$^{12}$ and R$^{13}$ are hydrogen or wherein Y is a group (e) carrying out a Mannich reaction with a compound of formula (II):

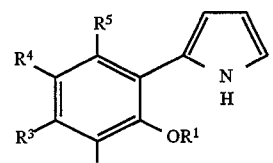  Formula II and an amine of formula (III), (IV) or (V):

  Formula (III)

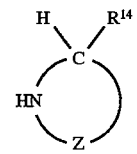  Formula (IV)

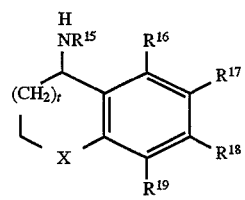  Formula (V)

in the presence of formaldehyde;

(b) to prepare a compound wherein Y is a group (a) wherein at least one of R$^7$ and R$^8$ is hydrogen, a group (c) wherein at least one of R$^{12}$ or R$^{13}$ is hydrogen, a group (e) or a group of formula (b) or (d) carrying out a Vilsmeier reaction with a compound of formula (II) and an amide of formula (VI) (VII) or (VIII):

  Formula (VI)

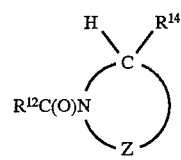  Formula (VII)

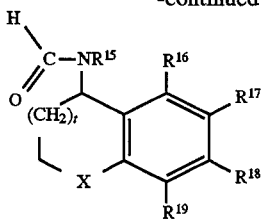

Formula (VIII)

or the appropriate oxo group of group (b) or (d) respectively, and reducing the intermediate product with, for example, sodium borohydride or cyanoborohydride;

(c) to prepare a compound wherein Y is a group (a) or (c) in which $R^7$, $R^8$, $R^{12}$ and $R^{13}$ are hydrogen or Y is a group (e) reductive amination of a compound of formula (IX):

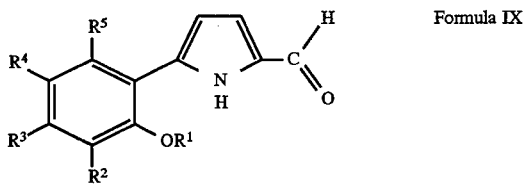

Formula IX with an amine of formula (III), (IV) or (V);
and optionally thereafter forming a salt of formula (I).

5. A method of treating a condition which requires modulation of a dopamine receptor which comprises administering to a subject in need thereof an effective amount of a compound of formula (I) according to claim 1 or a physiologically acceptable salt thereof.

6. A pharmaceutical composition comprising a compound of formula (I) according to claim 1 or a physiologically acceptable salt thereof and a physiologically acceptable carrier.

7. A method according to claim 5 wherein the dopamine receptor is a dopamine $D_3$ receptor.

8. A method according to claim 5 wherein a dopamine antagonist is required to modulate the receptor.

9. A method according to claim 5 wherein the condition is a psychotic condition.

10. An intermediate of formula (II):

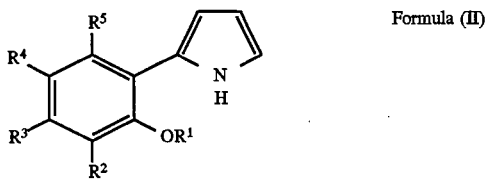

Formula (II)

wherein:

$R^1$ represents $C_{1-4}$alkyl;

$R^4$ represents a sulphonate group of formula $R^6OSO_2$ wherein $R^6$ is an optionally substituted aryl or optionally substituted heteroaryl group;

$R^2$, $R^3$ and $R^5$ each independently represent hydrogen, halogen, $C_{1-4}$alkyl, $C_{1-4}$alkoxy, $C_{1-4}$alkoxy$C_{1-4}$alkyl, $C_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-$C_{1-4}$alkylamino, trifluoromethyl, trifluoromethoxy, hydroxyl, hydroxy$C_{1-4}$alkyl, $C_{1-4}$alkylthio, $C_{1-4}$alkanoyl or $C_{1-4}$alkoxycarbonyl; or $R^1$ and $R^2$ together form a $C_{2-4}$alkyl chain, which chain is optionally substituted by one or two $C_{1-4}$alkyl groups, and $R^3$, $R^4$ and $R^5$ are as hereinbefore defined; or $R^2$ and $R^3$ together form a phenyl ring, in which case $R^4$ represents a group $R^6OSO_2$— as defined above and $R^5$ represents hydrogen.

11. An intermediate of formula (IX):

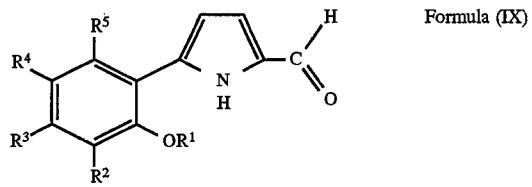

Formula (IX)

wherein:

$R^1$ represents $C_{1-4}$alkyl;

$R^4$ represents a sulphonate group of formula $R^6OSO_2$ wherein $R^6$ is an optionally substituted aryl or optionally substituted heteroaryl group;

$R^2$, $R^3$ and $R^5$ each independently represent hydrogen, halogen, $C_{1-4}$alkyl, $C_{1-4}$alkoxy, $C_{1-4}$alkoxy$C_{1-4}$alkyl, $C_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-$C_{1-4}$alkylamino, trifluoromethyl, trifluoromethoxy, hydroxyl, hydroxy$C_{1-4}$alkyl, $C_{1-4}$alkylthio, $C_{1-4}$alkanoyl or $C_{1-4}$alkoxycarbonyl; or $R^1$ and $R^2$ together form a $C_{2-4}$alkyl chain, which chain is optionally substituted by one or two $C_{1-4}$alkyl groups, and $R^3$, $R^4$ and $R^5$ are as hereinbefore defined; or $R^2$ and $R^3$ together form a phenyl ring, in which case $R^4$ represents a group $R^6OSO_2$— as defined above and $R^5$ represents hydrogen.

12. An intermediate of formula (X):

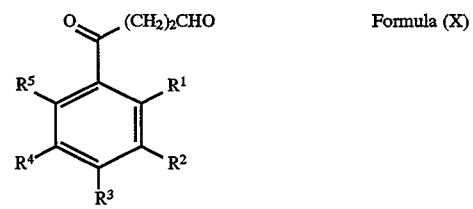

Formula (X)

wherein:

$R^1$ represents $C_{1-4}$alkyl;

$R^4$ represents a sulphonate group of formula $R^6OSO_2$ wherein $R^6$ is an optionally substituted aryl or optionally substituted heteroaryl group;

$R^2$, $R^3$ and $R^5$ each independently represent hydrogen, halogen, $C_{1-4}$alkyl, $C_{1-4}$alkoxy, $C_{1-4}$alkoxy$C_{1-4}$alkyl, $C_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-$C_{1-4}$alkylamino, trifluoromethyl, trifluoromethoxy, hydroxyl, hydroxy$C_{1-4}$alkyl, $C_{1-4}$alkylthio, $C_{1-4}$alkanoyl or $C_{1-4}$alkoxycarbonyl; or $R^1$ and $R^2$ together form a $C_{2-4}$alkyl chain, which chain is optionally substituted by one or two $C_{1-4}$alkyl groups, and $R^3$, $R^4$ and $R^5$ are as hereinbefore defined; or $R^2$ and $R^3$ together form a phenyl ring, in which case $R^4$ represents a group $R^6OSO_2$— as defined above and $R^5$ represents hydrogen.

* * * * *